US012292402B2

(12) United States Patent
Barlow

(10) Patent No.: US 12,292,402 B2
(45) Date of Patent: May 6, 2025

(54) MONITOR AND INDICATOR SYSTEM

(71) Applicant: David George Barlow, Jackson, WY (US)

(72) Inventor: David George Barlow, Jackson, WY (US)

(*) Notice: Subject to any disclaimer, the term of this patent is extended or adjusted under 35 U.S.C. 154(b) by 321 days.

(21) Appl. No.: 18/067,527

(22) Filed: Dec. 16, 2022

(65) Prior Publication Data

US 2023/0121751 A1  Apr. 20, 2023

Related U.S. Application Data

(63) Continuation-in-part of application No. 16/990,997, filed on Aug. 11, 2020, now Pat. No. 11,555,800.

(60) Provisional application No. 62/885,646, filed on Aug. 12, 2019.

(51) Int. Cl.
 *G01N 27/06* (2006.01)
 *G01N 33/18* (2006.01)
(52) U.S. Cl.
 CPC ............ *G01N 27/06* (2013.01); *G01N 33/18* (2013.01)
(58) Field of Classification Search
 CPC .. G01N 27/307; G01N 27/4166; G01N 27/06; G01N 27/4168; G01N 33/182; G01N 33/18; G01N 33/1826
 See application file for complete search history.

(56) References Cited

U.S. PATENT DOCUMENTS

| 4,802,255 A | 2/1989 | Breuer et al. |
| 4,872,235 A | 10/1989 | Nielsen |
| 5,218,304 A * | 6/1993 | Kinlen ............... G01N 27/4166 324/438 |

(Continued)

FOREIGN PATENT DOCUMENTS

| TW | 1774038 B | 8/2022 |
| WO | 2017184664 A1 | 10/2017 |

OTHER PUBLICATIONS

International Search Report and Written Opinion, dated Apr. 1, 2024, 11 pages, issued in International Application No. PCT/US2023/083971.

(Continued)

*Primary Examiner* — Gurpreet Kaur
(74) *Attorney, Agent, or Firm* — AVEK IP, LLC

(57) ABSTRACT

A method of monitoring a concentration of sanitizer in a solution includes providing a device that includes a plurality of sensors. The method continues by executing, via the device, a calibration stage that includes placing the device in sanitizer-free water, wherein the device: determines a temperature of the water; conducts a water analysis; and measures, via at least one sensor, a baseline resistance of the water. Sanitizing compounds are added to the water; and the device executes an operational stage, wherein the device: determines a resistance of the water with the sanitizing compounds; calculates a concentration of the sanitizing compounds in the water, wherein the concentration is based on the temperature of the water, the water analysis, and the baseline resistance; compares the calculated concentration to a predetermined threshold concentration; and activates an indication module of the device based on the comparison of the calculated concentration to the predetermined concentration.

20 Claims, 12 Drawing Sheets

(56) References Cited

U.S. PATENT DOCUMENTS

| | | | |
|---|---|---|---|
| 5,248,403 | A | 9/1993 | Tomita et al. |
| 5,683,655 | A | 11/1997 | Carter |
| 6,794,318 | B2 | 9/2004 | Anderson et al. |
| 8,481,470 | B2 | 7/2013 | Jones, Jr. |
| 8,518,704 | B2 | 8/2013 | Campbell et al. |
| 9,347,906 | B2 | 5/2016 | Gruden |
| 9,492,058 | B2 | 11/2016 | Albright |
| 9,510,668 | B2 | 12/2016 | Patel et al. |
| 9,776,888 | B1 | 10/2017 | Kurani et al. |
| 9,829,471 | B2 | 11/2017 | Hammond et al. |
| 2003/0059483 | A1* | 3/2003 | Sowle .................. C11D 3/3955 424/661 |
| 2003/0211011 | A1 | 11/2003 | Phillips et al. |
| 2008/0048674 | A1 | 2/2008 | Tan et al. |
| 2012/0145561 | A1 | 6/2012 | Coulon et al. |
| 2013/0005048 | A1 | 1/2013 | Felten et al. |
| 2013/0065257 | A1 | 3/2013 | Wang et al. |
| 2013/0214797 | A1 | 8/2013 | Gruden |
| 2015/0115983 | A1 | 4/2015 | Potyrailo et al. |
| 2015/0352210 | A1 | 12/2015 | Wang et al. |
| 2015/0374868 | A1 | 12/2015 | Bruce et al. |
| 2016/0116418 | A1 | 4/2016 | Clark |
| 2017/0007731 | A1 | 1/2017 | Sharma |
| 2021/0048409 | A1 | 2/2021 | Barlow |
| 2021/0316056 | A1 | 10/2021 | Szpara et al. |
| 2023/0121751 | A1 | 4/2023 | Barlow |

OTHER PUBLICATIONS

International Search Report and Written Opinion, dated Dec. 7, 2020, 9 pages, issued in International Application No. PCT/US2020/045825.

Notice of Allowance, dated Jun. 6, 2022, 2 pages, issued in Taiwan patent application No. 109127388; foreign associate reporting letter included, 2 pages.

Office Action, dated Jul. 5, 2021, 6 pages, issued in Taiwanese Application No. 109127388.

* cited by examiner

Water Source: LS #1  Hardness: 28  Water pH:  Test Date:
TDS:  EC:

| Target PPM | Actual PPM | COLD test (21.1C / 70 F) | | | WARM test (37.8C / 100F) | | | HOT test (54.4C / 130F) | | | Grams |
|---|---|---|---|---|---|---|---|---|---|---|---|
| | | Count | Solution temp | Thermo temp | Count | Solution temp | Thermo temp | Count | Solution temp | Thermo temp | |
| 450 | 456.4 | 1920 | | 21.1 | 1485 | | 37.8 | 1135 | | 57.2 | |
| 350 | 359.2 | 2135 | | 20.6 | 1685 | | 37.8 | 1365 | | 52.8 | |
| 250 | 255.7 | 2318 | | 20.6 | 1790 | | 38.3 | 1498 | | 51.7 | |
| 150 | 156.3 | 2650 | | 20.6 | 2070 | | 38.9 | 1755 | | 49.4 | |
| RAW | | 3280 | | 20.6 | 2595 | | 38.3 | 2315 | | 51.7 | |

Water Source: DS #1  Hardness: 194  Water pH:  Test Date:
TDS:  EC:

| Target PPM | Actual PPM | COLD test (21.1C / 70 F) | | | WARM test (37.8C / 100F) | | | HOT test (54.4C / 130F) | | | Grams |
|---|---|---|---|---|---|---|---|---|---|---|---|
| | | Count | Solution temp | Thermo temp | Count | Solution temp | Thermo temp | Count | Solution temp | Thermo temp | |
| 450 | 435.1 | 739 | | 21.1 | 564 | | 37.8 | 417 | | 48.9 | |
| 350 | 340.6 | 770 | | 20.6 | 612 | | 35.6 | 480 | | 51.7 | |
| 250 | 245 | 800 | | 20.6 | 622 | | 36.7 | 487 | | 52.8 | |
| 150 | 162.8 | 830 | | 20 | 629 | | 36.7 | 525 | | 51.7 | |
| RAW | | 905 | | 20.6 | 685 | | 37.8 | 545 | | 52.2 | |

Water Source: LS #2  Hardness: 28  Water pH:  Test Date:
TDS:  EC:

| Target PPM | Actual PPM | COLD test (21.1C / 70 F) | | | WARM test (37.8C / 100F) | | | HOT test (54.4C / 130F) | | | Grams |
|---|---|---|---|---|---|---|---|---|---|---|---|
| | | Count | Solution temp | Thermo temp | Count | Solution temp | Thermo temp | Count | Solution temp | Thermo temp | |
| 450 | 414 | 1998 | | 19.4 | 1490 | 21.1 | 40.4 | 1250 | 25.3 | 53.2 | |
| 350 | 316.1 | 2220 | | 19.4 | 1560 | 23.7 | 44.8 | 1383 | 24.9 | 53.2 | |
| 250 | 235.6 | 2430 | | 19.6 | 1765 | 24.5 | 42.7 | 1575 | 23.5 | 51.8 | |
| 150 | 143.5 | 2676 | | 19.7 | 2138 | 17.6 | 38.3 | 1755 | 24.5 | 53 | |
| RAW | | 3480 | | 18.6 | 2440 | 22.5 | 45 | 2130 | 27.5 | 55.2 | |

Water Source: FGS #4  Hardness: 203  Water pH:  Test Date:
TDS:  EC:

| Target PPM | Actual PPM | COLD test (21.1C / 70 F) | | | WARM test (37.8C / 100F) | | | HOT test (54.4C / 130F) | | | Grams |
|---|---|---|---|---|---|---|---|---|---|---|---|
| | | Count | Solution temp | Thermo temp | Count | Solution temp | Thermo temp | Count | Solution temp | Thermo temp | |
| 450 | 397.3 | 582 | 16.1 | 19.8 | 410 | 22.6 | 39.8 | 323 | 28.5 | 55.6 | |
| 350 | 303.1 | 592 | 16.2 | 19.7 | 406 | 22.4 | 41.3 | 327 | 27.3 | 55.5 | |
| 250 | 223.2 | 604 | 16.4 | 19.7 | 439 | 23.1 | 38.0 | 340 | 26.2 | 53.9 | |
| 150 | 136.2 | 617 | 16.5 | 19.9 | 419 | 22.9 | 41.7 | 358 | 25.4 | 52.1 | |
| RAW | | 675 | 17.3 | 19.5 | 398 | 18.2 | 48.6 | 374 | 21.9 | 51.6 | |

FIG. 11a

Water Source: BLS #2  Hardness: 238  Test Date:
TDs:  Water pH:
EC:

| Target | Actual | | COLD test (21.1C / 70 F) | | | WARM test (37.8C / 100F) | | | HOT test (54.4C / 130F) | | |
|---|---|---|---|---|---|---|---|---|---|---|---|
| PPM | PPM | Count | Solution temp | Thermo temp | Count | Solution temp | Thermo temp | Count | Solution temp | Thermo temp | Grams |
| 450 | 402.7 | 1036 | 16.2 | 19.5 | 712 | 23.0 | 42.2 | 608 | 27.5 | 52.0 | |
| 350 | 306.9 | 1087 | 16.2 | 19.4 | 767 | 22.7 | 40.4 | 628 | 28.3 | 53.3 | |
| 250 | 220.8 | 1129 | 16.4 | 19.4 | 773 | 21.6 | 42.6 | 638 | 26.9 | 55.3 | |
| 150 | 132.3 | 1167 | 16.5 | 19.6 | 850 | 20.6 | 38.6 | 689 | 25.2 | 53.0 | |
| RAW | | 1243 | 17.1 | 19.6 | 855 | 17.1 | 43.8 | 755 | 22.5 | 53.0 | |

Water Source: RW #1  Hardness: 88  Test Date:
TDs:  Water pH:
EC:

| Target | Actual | | COLD test (21.1C / 70 F) | | | WARM test (37.8C / 100F) | | | HOT test (54.4C / 130F) | | |
|---|---|---|---|---|---|---|---|---|---|---|---|
| PPM | PPM | Count | Solution temp | Thermo temp | Count | Solution temp | Thermo temp | Count | Solution temp | Thermo temp | Grams |
| 450 | 409.6 | 1414 | 15.6 | 19.2 | 1060 | 21.1 | 38.5 | 897 | 25.9 | 50.5 | |
| 350 | 322.3 | 1495 | 15.7 | 19.3 | 1146 | 21.9 | 35.6 | 923 | 26.5 | 50.7 | |
| 250 | 228.2 | 1596 | 15.8 | 19.2 | 1154 | 22 | 40.2 | 962 | 26.5 | 54.2 | |
| 150 | 136.5 | 1707 | 15.9 | 19.2 | 1236 | 20.1 | 41.5 | 1032 | 25.3 | 54.1 | |
| RAW | | 1887 | 16.6 | 19.1 | 1350 | 16.2 | 44.1 | 1164 | 21.9 | 54.5 | |

Water Source: RPS #2  Hardness: 72  Test Date:
TDs:  Water pH:
EC:

| Target | Actual | | COLD test (21.1C / 70 F) | | | WARM test (37.8C / 100F) | | | HOT test (54.4C / 130F) | | |
|---|---|---|---|---|---|---|---|---|---|---|---|
| PPM | PPM | Count | Solution temp | Thermo temp | Count | Solution temp | Thermo temp | Count | Solution temp | Thermo temp | Grams |
| 450 | 401.9 | 1452 | 16 | 19 | 1106 | 21.1 | 36.7 | 866 | 27.4 | 52 | |
| 350 | 318.2 | 1556 | 16 | 18.9 | 1165 | 20.8 | 37.6 | 906 | 26.6 | 54.4 | |
| 250 | 231 | 1621 | 16.1 | 19 | 1220 | 20.4 | 37.9 | 970 | 24.9 | 53.4 | |
| 150 | 134.2 | 1744 | 16.3 | 18.9 | 1335 | 19.6 | 37.4 | 1074 | 24.2 | 53.2 | |
| RAW | | 1968 | 16.8 | 18.8 | 1488 | 17 | 39.4 | 1233 | 20.8 | 53.1 | |

FIG. 11b

MONITOR AND INDICATOR SYSTEM

CROSS-REFERENCE TO RELATED APPLICATIONS

This application is a continuation-in-part of U.S. application Ser. No. 16/990,997, filed Aug. 11, 2020, which claims the benefit of priority of U.S. Provisional Patent Application No. 62/885,646, filed Aug. 12, 2019, the disclosure of each of which is incorporated by reference herein in its entirety.

FIELD OF THE DISCLOSURE

The disclosure relates generally to the field of sanitization monitoring and indication. More specifically, the disclosure relates to the field of a monitor and indicator system for sanitization systems.

BACKGROUND

Sanitization systems are used to reduce the presence of microorganisms on a surface. Microorganism growth can occur when utensils are improperly cleaned, or are not cleaned in a timely manner which may cause adverse effects to the public. Food surfaces that contact food that has not been prepared or refrigerated properly can contaminate other food, causing harmful effects if ingested. Thus, maintaining clean and sanitized food contact surfaces, such as knives and other utensils, is an integral part of the food service industry.

Different chemical substances may be utilized as sanitizing agents in sanitizing solutions. Commonly used chemical substances include, among others, chlorine (bleach), quaternary ammonium, and iodine. Sanitizing solutions with one or more of these chemical substances must be changed regularly in sanitization processes because the concentration of these chemical substances decreases over time, thus eventually losing the sanitizing effects. Laws, regulations, and/or policies often require the concentration of the sanitizing chemical substances to be within certain ranges to assure the desired sanitization effects. For example, a chlorine sanitizing solution is usually required to have a concentration of 50 to 200 parts per million (ppm) chlorine; a quaternary ammonium sanitizing solution is usually required to have a concentration of 100 to 400 ppm quaternary ammonium; and an iodine sanitizing solution is usually required to have a concentration of 5 to 50 ppm iodine.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

According to one embodiment of the invention, a monitor and indicator system includes a sensor part, a control and indication part, and a power part. The monitor and indicator system is configured to: (a) monitor a concentration of a sterilant in a sanitizing solution; (b) determine a depletion of the sterilant upon detecting that the concentration of the sterilant becomes equal to or falls below a predetermined threshold concentration level; and (c) indicate the depletion of the sterilant of the sanitizing solution by emitting a notification.

According to another embodiment of the invention, a method for monitoring a concentration of a sanitizing chemical substance in a sanitizing solution includes: (a) providing a container; (b) filling the container with a sanitizing solution comprising a sterilant; (c) placing a monitor and indicator system having a sensor part, a control and indication part, and a power part in the container; (d) activating the monitor and indicator system to measure a concentration of the sterilant; (e) activating the monitor and indicator system to emit a first notification when a measured concentration of the sterilant in the sanitizing solution is above a predetermined threshold concentration level; (f) activating the monitor and indicator system to emit a second notification to indicate a depleted sanitizing solution when the measured concentration of the sterilant in the sanitizing solution becomes equal to or falls below the predetermined threshold concentration level; (g) replacing the depleted sanitizing solution with a new batch of sanitizing solution having a concentration of the sterilant above the predetermined threshold concentration level; (h) disposing the monitor and indicator system; and (i) placing a new monitor and indicator system in the kitchen container with the new batch of sanitizing solution.

In yet another embodiment, a device for monitoring a concentration of sanitizing compounds in water includes a power module, a sensor part comprising a plurality of sensors, and a control and indicator part. The control and indicator part includes a processor in operable communication with an indication module and non-transitory computer memory having programming. The programming, when executed by the processor, performs the following steps: (1) executes a calibration stage that includes (i) determining, via at least one sensor of the plurality of sensors, a temperature of a sample of water from a water source, the sample of water being devoid of sanitizing compounds; (ii) measuring, via at least one sensor of the plurality of sensors, a characteristic of the sample of water; and (iii) measuring, via at least one sensor of the plurality of sensors, a baseline resistance of the sample of water; and (2) executing an operational stage that includes (iv) determining a resistance of a sanitizing solution, wherein the sanitizing solution comprises water from the water source and at least one sanitizing compound; (v) calculating a concentration of the sanitizing solution, wherein the concentration is based on the temperature of the water sample, the characteristic of the water sample, and the baseline resistance of the water sample; (vi) comparing the calculated concentration to a predetermined threshold concentration stored in the memory; and (vii) activating the indication module based on the comparison of the calculated concentration to the predetermined concentration.

According to still yet another embodiment, a method of monitoring a concentration of sanitizer in a solution includes first providing a device for monitoring a concentration of a sanitizing solution that includes a plurality of sensors. The method continues by executing, via the device, a calibration stage that includes placing the device in water, the water being devoid of sanitizer, wherein the device: determines a temperature of the water; conducts a water analysis; and measures, via at least one sensor of the plurality of sensors, a baseline resistance of the water. Sanitizing compounds are added to the water; and the device executes an operational stage, wherein the device: determines a resistance of the water with the sanitizing compounds; calculates a concentration of the sanitizing compounds in the water, wherein the concentration is based on the temperature of the water, the water analysis, and the baseline resistance; compares the calculated concentration to a predetermined threshold concentration; and activates an indication module of the device based on the comparison of the calculated concentration to the predetermined concentration.

In a further embodiment, a method of monitoring a concentration of sanitizing compounds in a solution includes first providing a device for monitoring a concentration of a sanitizing solution. The device includes a power module; a sensor part comprising a plurality of sensors; and a control and indicator part. The method continues by executing a calibration stage that includes placing the device in water, the water being devoid of sanitizer. In the water, the device: determines a temperature of the water; measures, via at least one sensor of the plurality of sensors, a value of electrical conductivity of the water; and measures, via at least one sensor of the plurality of sensors, a baseline resistance of the water. The method continues by adding at least one sanitizing compound to the water and executing an operational stage. In the operational stage, the device: determines a resistance of the water with the at least one sanitizing compound; calculates a concentration of the at least one sanitizing compound in the water, wherein the concentration is based on the temperature of the water, the electrical conductivity of the water, and the baseline resistance of the water; compares the calculated concentration to a predetermined threshold concentration; and activates the indication module based on the comparison of the calculated concentration to the predetermined concentration.

BRIEF DESCRIPTION OF THE DRAWINGS

Illustrative embodiments of the invention are described in detail below with reference to the attached figures.

FIGS. 11a and 11b illustrate various test results from experiments conducted for monitoring a sanitizing solution.

DETAILED DESCRIPTION

All states have food services codes and regulations that prescribe acceptable methods and times for cleaning utensils (e.g., knives, spoons, forks, etc.) The regulations usually require the concentration of the sanitizing chemical substances to be within certain ranges to assure the desired sanitization effects. However, maintaining this appropriate level of cleanliness relies on the dedication and common sense of those persons responsible for ensuring that the codes and regulations are being complied with. For example, while a chlorine sanitizing solution is very effective in killing bacteria and other microbes and preventing contamination in food industries, the chlorine concentration of the solution decreases over time, thus losing the sanitizing effects after being exposed to materials such as food waste. If no one is checking the concentration of the solution, then the solution may not be effective to sanitize the utensils.

Depending on the foodstuffs that the utensil contacts, the utensil may need to be cleansed very frequently with a sanitizing solution. Thus, sanitation processes can often be laborious and time intensive, and the sanitizing solutions may be depleted quickly, which is especially inconvenient during high service periods, such as lunch and dinner. In some cases, food industry personnel may not always be able to timely use traditional chlorine test strips to measure the chlorine concentration of the chlorine sanitizing solutions, and thus may not be able to timely replace depleted chlorine sanitizing solutions. Accordingly, it may be desirable to have a simple, automatic, reliable, and low-cost monitor and indicator system to better remind the food industry personnel and notify them of the depleted chlorine sanitizing solutions which need to be replaced. Other sanitizing chemical substances suffer from the same or similar drawbacks.

Figure 1:
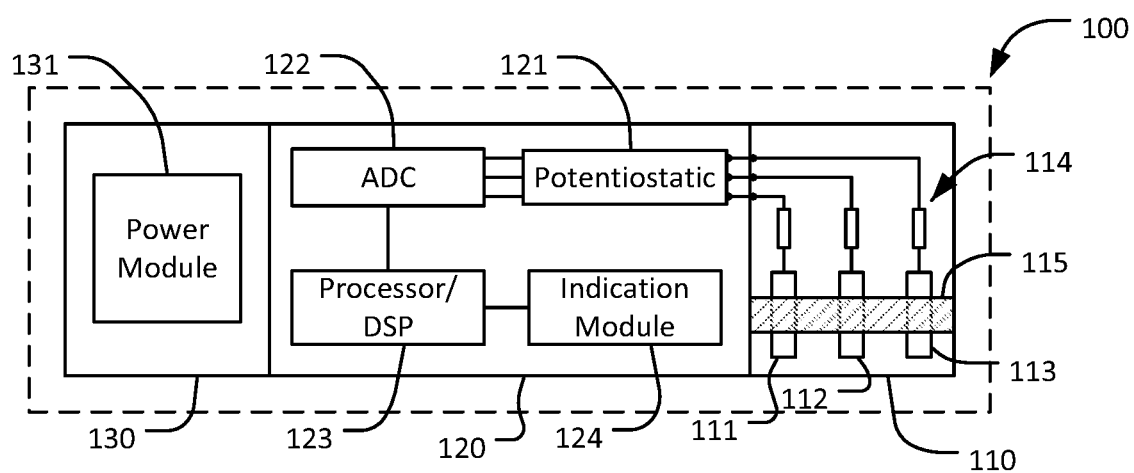
FIG. 1 shows an embodiment of a monitor and indicator system.

Embodiments of systems and methods for monitoring the efficacy of sanitizing solutions are illustrated in FIGS. 1-7. Referring first to FIG. 1, in some embodiments, a monitor and indicator system 100 may generally include a sensor part 110, a control and indication part 120, and a power part 130. The sensor part 110 may include a disposable screen-printed electrode system, which can be a multi-electrode system such as a two-electrode system, a three-electrode system, a four-electrode system, et cetera. In the three-electrode system shown in FIG. 1, the disposable screen-printed electrode system may include a counter electrode 110, a working electrode 120, and a reference electrode 130. The sensor part 110 may be covered (or laminated in some embodiments) with a top insulation layer 114 having an opening 115 to concurrently expose parts of the counter electrode 110, working electrode 120, and reference electrode 130 while sealing off the remaining parts of the sensor part 110 from the external environment (e.g., gas, liquid, solid). The control and indication part 120 may include a potentiostatic module 121, an analog/digital converter module 122, a processor module 123, and an indication module 124. The power part 130 may include a power module 131.

As will be described in greater detail below, in embodiments, the sensor part 110, the control and indication part 120, and the power part 130 may be manufactured separately and configured to be connected together. One or more of the parts 110, 120, and/or 130 may be configured as a sticker which may be disposed on the side of a container. In other embodiments, the various parts 110, 120, and 130 may be manufactured together as a single disposable and configurable monitor and indicator system 100, which may, but need not be, a sticker.

In any event, a user may place the system 100 inside of a vessel having the sanitizing solution therein. The concentration of the sanitizing solution will gradually decrease over time with use. The sensor part 110 may determine the concentration of the sanitizing agent (e.g., chlorine) in the sanitizing solution in real time as described herein. When the indication module 124 is activated, a user knows that the concentration of a sanitizing solution is below the lower limit, and it is time to replace the depleted sanitizing solution with a new batch of sanitizing solution having a concentration of the sanitizing chemical substance above the predetermined threshold concentration level. If the system 100 is disposable, a new sticker 100 may be disposed into the new batch of the sanitizing solution, or the disposable portion of the system 100 may be replaced.

Figure 2:
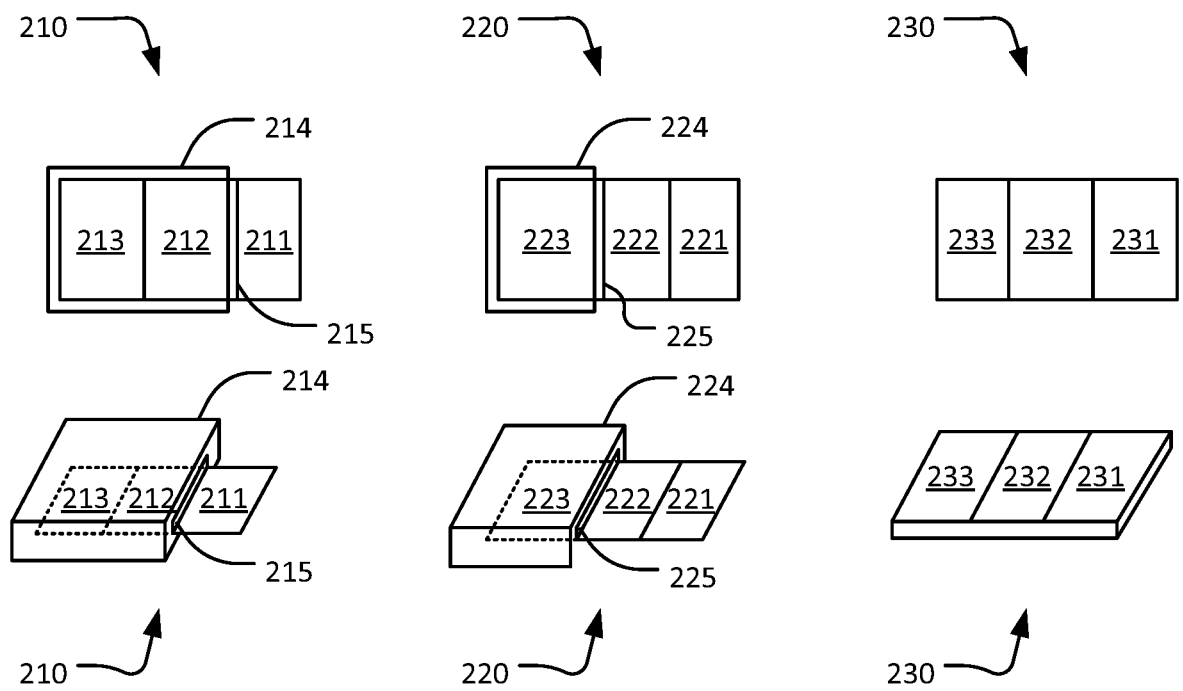
FIG. 2 shows exemplary embodiments of monitor and indicator systems.

FIG. 2 shows the monitor and indicator system 100 according to various embodiments. In embodiment 210, the control and indication part 212, and the power part 213 of the monitor and indicator system 100 may be enclosed within an external housing 214 configured to connect to the sensor part 211 of the monitor and indicator system 100 by a connection socket 215. In this embodiment 210, the sensor part 211 of the monitor and indicator system 100 may be disposable, and may be replaced after a single test, multiple tests, or a period of predetermined testing time. The control and indication part 212 and the power part 213 enclosed within the external housing 214 may be either disposable or permanent. And in some embodiments, this external housing 214 may be free or fixed inside or outside a sanitizing solution.

In embodiment 220, the sensor part 221 and the control and indication part 222 of the monitor and indicator system 100 may be manufactured together as an integral disposable piece which may be replaced after a single test, multiple tests, or a period of predetermined testing time. This disposable piece including the sensor part 221 and the control and indication part 222 may be connected to the power part 223 by a connection socket 225. The power part 223 of the monitor and indicator system 100 may be enclosed in an external housing 224. And in some embodiments, this external housing 224 may be free or fixed inside or outside a sanitizing solution.

In embodiment 230, the sensor part 231, the control and indication part 232, and the power part 233 may be altogether manufactured as an integral single piece, and act as a disposable monitor and indicator system 100 which may be a sticker and may be disposed after a single test, multiple tests, or a period of predetermined testing time. As with embodiments 210 and 220, in embodiment 230, the disposable monitor and indicator system 100 may be free or fixed inside or outside a sanitizing solution.

While only three embodiments 210, 220, and 230 of the monitor and indicator system 100 are shown in FIG. 2, it is to be understood that the sensor part 231, the control and indication part 232, and the power part 233 of the monitor and indicator system 100 may be individually or in combination manufactured as disposable or permanent pieces. In addition, they may also individually or in combination function as disposable or permanent pieces.

Figure 3:
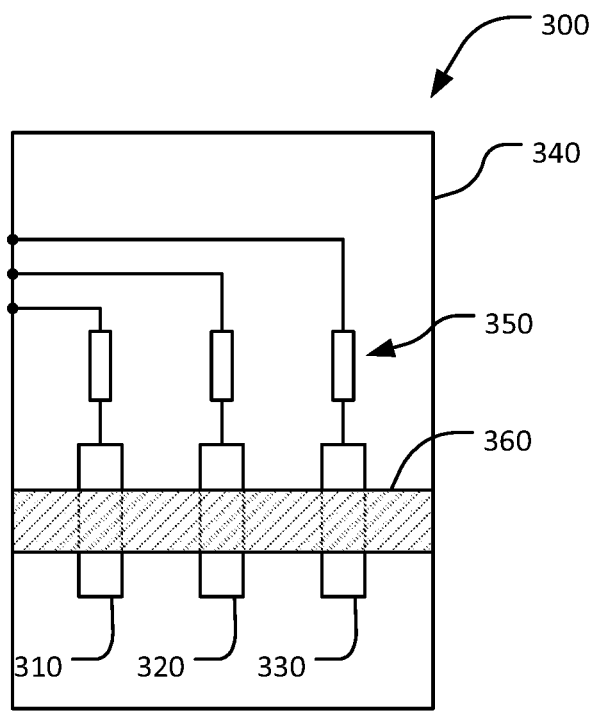
FIG. 3 shows an exemplary embodiment of a disposable screen-printed electrode.

Moving on, FIG. 3 shows a disposable screen-printed electrode 300 which may individually or in combination function as the sensor part 110 of the monitor and indicator system 100. A disposable screen-printed electrode 300 may include a counter electrode 310, a working electrode 320, and a reference electrode 330. These electrodes may be individually or in combination made of materials such as platinum, palladium, gold, silver, silver chloride, potassium chloride, nickel, aluminum, calcium, cesium, bromine, lithium, molybdenum, copper, zinc, cobalt, brass, titanium, thorium, zirconium, lanthanum, cerium, ruthenium, iridium, manganese, cadmium, indium tin oxide, graphite, graphene, carbon, lead, pencil lead, ceramic, plastics, polymers, nanotubes, nanowires, nanorods, boron-doped diamond, diamond, ferrocene, benzethonium chloride, and mixed metal oxides including oxides of precious metals ruthenium, iridium, platinum, and titanium.

The disposable screen-printed electrode 300 may further include a substrate film 340 on which the counter electrode 310, the working electrode 320, and the reference electrode 330 are disposed. The substrate film 340 may be individually or in combination made of materials such as glass, aluminum, ceramic, metal, paper, wax, silicon, silicon carbide, polyester, cyclic olefin copolymer, polyethylene, polyethylene terephthalate, polypropylene, polystyrene, polyvinyl chloride, polyvinylidene chloride, polyvinylidene difluoride, polyamide, polyimide, polychlorotrifluoroethylene, polycarbonate, polyurethane, acrylonitrile butadiene styrene, polyacetylene, polytetrafluoroethylene, phenolics, polyimide, polysulfone, polypyrrole, para-aramid, polychloroprene, polyaniline, polythiophene, polyvinylpyrrolidone, polystyrenesulfonate, polyacrylonitrile, phenol-formaldehyde resin, furan, silicone, polymethylmethacrylate, ethyl cellulose, polyether ether ketone, polyethylene naphthalate, and other suitable polymeric materials. In some embodiments, the substrate film may be a rigid or flexible tape. Preferably, the substrate film 340 is configured to survive in temperatures ranging from about −20° C. (−4° F.) to about 150° C. (302° F.).

An insulation layer 350 with an opening 360 may be provided on top of the substrate film 340, covering the electrodes 310, 320, and 330. While the opening 340 of the insulation layer 350 shown in FIG. 3 has a rectangular configuration, it is to be understood that this opening 340 may be in any shape so long as it concurrently exposes parts of the counter electrode 310, working electrode 320, and reference electrode 330 while sealing off the remaining parts of the disposable screen-printed electrode 300 from the external environment (e.g., gas, liquid, solid).

Figure 4:
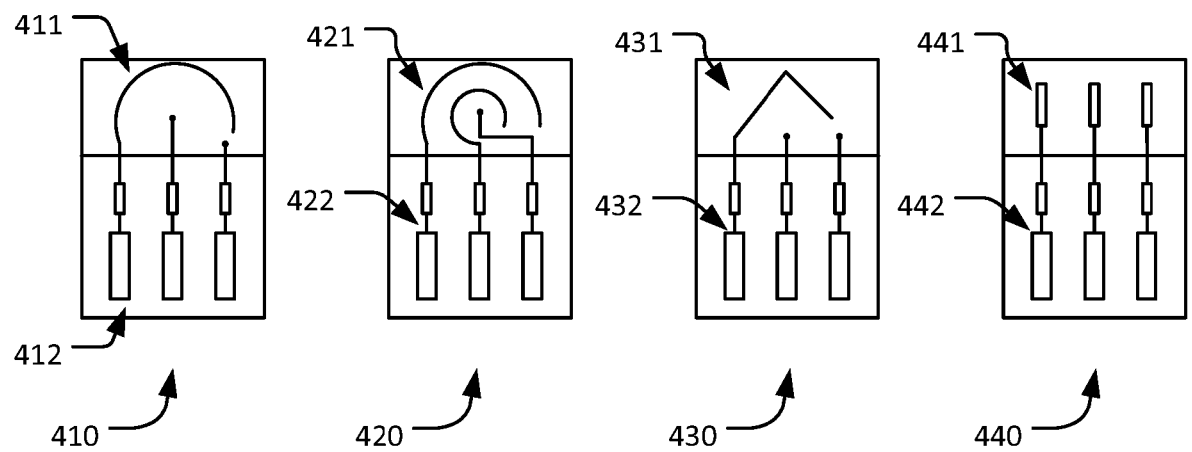
FIG. 4 shows embodiments of disposable screen-printed electrodes.

FIG. 4 shows some further exemplary embodiments 410, 420, 430, and 440 of the disposable screen-printed electrode 110. The screen-printed electrodes in embodiments 410, 420, 430, and 440 all include three-electrodes each having its own arrangement of electrode shapes.

The electrodes may be configured to measure voltage and current within the solution. Depending on the results, it may be possible to determine whether the solution is within an acceptable range, and therefore, whether the solution needs to be changed.

In embodiments, the screen-printed electrode 110 may be replaced with a chemically sensitive field-effect transistor (ChemFET). The ChemFET may be used as a sensor for measuring chemical concentration of the sanitizing solution. As the chemical concentration of the sanitizing solution changes, the current through the transistor changes accordingly.

Figure 5:
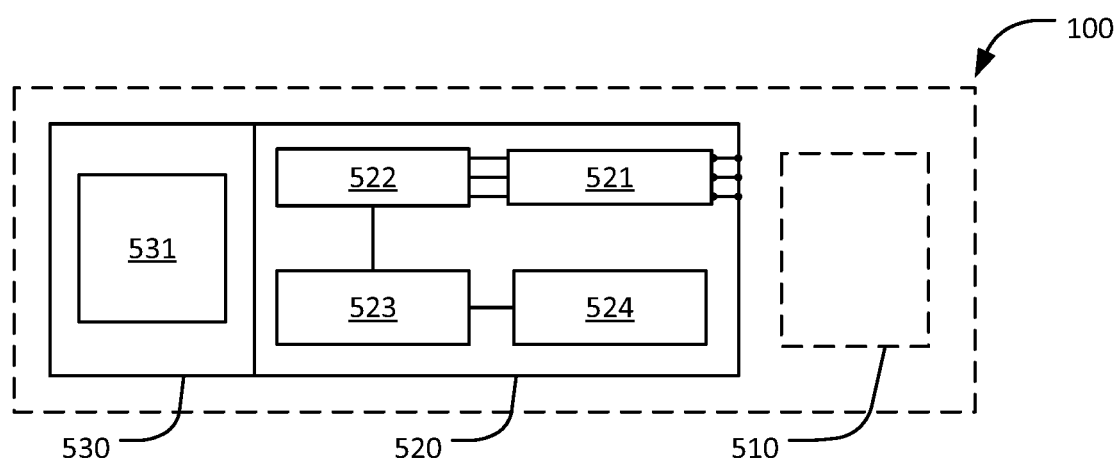
FIG. 5 shows an exemplary embodiment of a power part and a control and indication part of a monitor and indicator system.

FIG. 5 illustrates an embodiment of the control and indication part 520 (corresponding generally to the control and indication part 120 in FIG. 1) and the power part 530 (corresponding generally to the power part 130) of a monitor and indicator system 100. The control and indication part 520 may include a potentiostatic module 521, an analog/digital converter module 522, a processor module 523, and an indication module 524. In some embodiments, the potentiostatic module 521 may receive electrochemical signals from the disposable screen-printed electrode in a sensor part 510 (corresponding generally to the sensor part 110, and also described as embodiments 300, 410, 420, 430, and 440). And the potentiostatic module 521 may be in further electrical connection with the processor 523 via an analog-digital converter 522. The analog-digital converter 522 may convert the analog signals received from the potentiostatic module 521 to digital signals, and then send the converted digital signals to the processor 523. Depending on the received digital signals from the analog-digital converter 522, the processor 523 may decide if the measured concentration of the sanitizing solution is above a target range, within the target range, or below the target range, and then actuate the indication module 520 accordingly based on the concentration measurements, as will be described in greater detail below. The processor 523 may cause the indication module 524 to (1) activate a low power lighting source 605 (examples shown in FIGS. 6A & 6B) to provide one or more alert notification(s) to a user; (2) activate a transmission module within it to transmit one or more alert notification(s) wirelessly or by-wire to a remote device; (3) activate a mechanical mechanism within it to release a notification dye of a specific color; and/or (4) activate a speaker to play a notification message, for example. The power part 530 of the monitor and indicator system 100 may include a power module 531 which can be a battery (which may be configured to have a certain predefined shelf-life), an internal electrochemical source powered by chemical energy or electrochemical energy, a power interface in wired or wireless connection with an external power source, or any other means of providing the necessary power to the system, whether now known or later developed.

In some embodiments, the indication module 524 may include one or more low power lighting source such as an ultra-low power light-emitting diode (LED), a low-power lamp, a low-power light bulb, or a low-power luminescent light source. In an example, the indication module may include one or more red ultra-low power LED units which can be activated when the concentration of the sanitizing solution is equal to or falls below a predetermined concentration threshold level. The indication module 524 may further include one or more green ultra-low power LED units which can be activated when the concentration of the sanitizing solution is above a predetermined concentration threshold level.

In other embodiments, the indication module 524 may include a transmission module configured to transmit an alert notification (e.g., wirelessly) to a remote device. In an example, the indication module 524 may be activated to transmit a wireless notification to a remote device when the concentration of the sanitizing solution becomes equal to or falls below a predetermined concentration threshold level. Optionally, the indication module 524 may transmit notifications at predetermined intervals indicating the real-time chlorine concentration of the chlorine sanitizing solution or merely notifications that the concentration is above/below the threshold to a remote device. Optionally, the notifications may be exact concentrations.

In further embodiments, the indication module 524 may include a mechanical mechanism to release a dye into the sanitizing solution. Depending on different applications, a single dye or a combination of multiple dyes may be used. For example, a non-reactive food dye may be released and dissolved in the sanitizing solution when the concentration becomes equal to or falls below a predetermined concentration threshold level. A user can therefore easily detect that the sanitizing solution is depleted and needs to be replaced.

In another embodiment, a non-reactive dye may be released in the monitor and indicator system 100, instead of being released and dissolved into the sanitizing solution. Of course, both reactive and non-reactive dyes may be used individually or in combination.

While the above embodiments illustrate some specific configurations of the monitor and indicator system 100, it is to be understood that there may be other configurations which may be capable of implementing similar functions and/or achieving similar results. For example, it should be understood that in some embodiments, the control and indication part 520 (generally 120) and the power part 530 (generally 130) may be manufactured together, enclosed within an external housing, and in connection with the sensor part 510 (generally 110) of the monitor and indicator system 100 by a connection socket. In this case, the sensor part 510 of the monitor and indicator system 100 may be disposable, and it may be replaced after a single test, multiple tests, or a period of predetermined testing time. The control and indication part 520 and the power part 530 enclosed within the external housing may be either disposable or permanent. A user may thus replace the sensor part 510 upon replacing a depleted solution with a new batch of solution without throwing away the external housing enclosing the control and indication part 520 and the power part 530. In other embodiments, the control and indication part 520 and the sensor part 510 may be manufactured together as the disposable portion in connection with the power part 530 via a connection socket. And the power part 530 may be on its own enclosed within another external housing. In this case, the user may replace the disposable portion containing the sensor part 510 and the control and indication part 520 each time when the depleted solution is replaced with a new batch of solution without throwing away the power part 530.

Figure 6A:
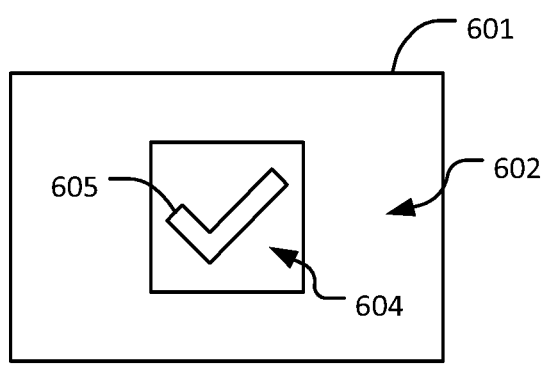
FIGS. 6A and 6B show embodiments of monitor and indicator systems with various external indication functions.
Figure 6B:
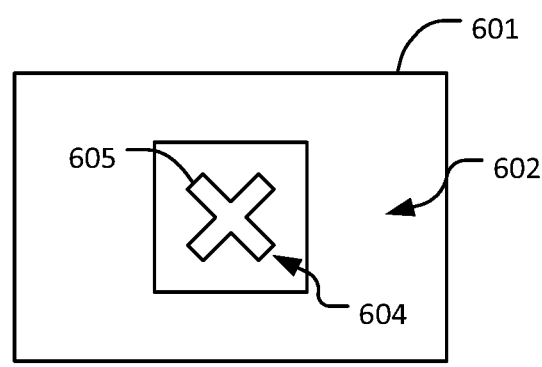

Moving on, FIGS. 6A and 6B illustrate further embodiments of the monitor and indicator system 100 with various external indication functions to indicate the acceptable and/or unacceptable status of the sanitizing solution based on whether the measured concentration level of the sanitizing solution is above a predetermined concentration threshold level. As shown in FIGS. 6A and 6B, the monitor and indicator system 100 may include a substrate film layer 601 and an insulation layer 602. The insulation layer 602 may include a display area 604 configured to display a notification 605. In some examples, e.g., as shown in FIG. 6A, the display area 604 may be activated to display a check mark 605 when the concentration of the sanitizing solution is above a predetermined concentration threshold level. And the check mark may be of a color, such as green, which is easily recognizable as a color that indicates that the status is "good." In other examples, e.g., as shown in FIG. 6B, the display area 604 of the monitor and indicator system 100 may be activated to display a cross mark 605 when the concentration of the sanitizing solution becomes equal to or falls below a predetermined concentration threshold level. And the cross mark may be of a color, such as red, which is easily recognizable as a color that indicates that the status is "bad."

Figure 7:
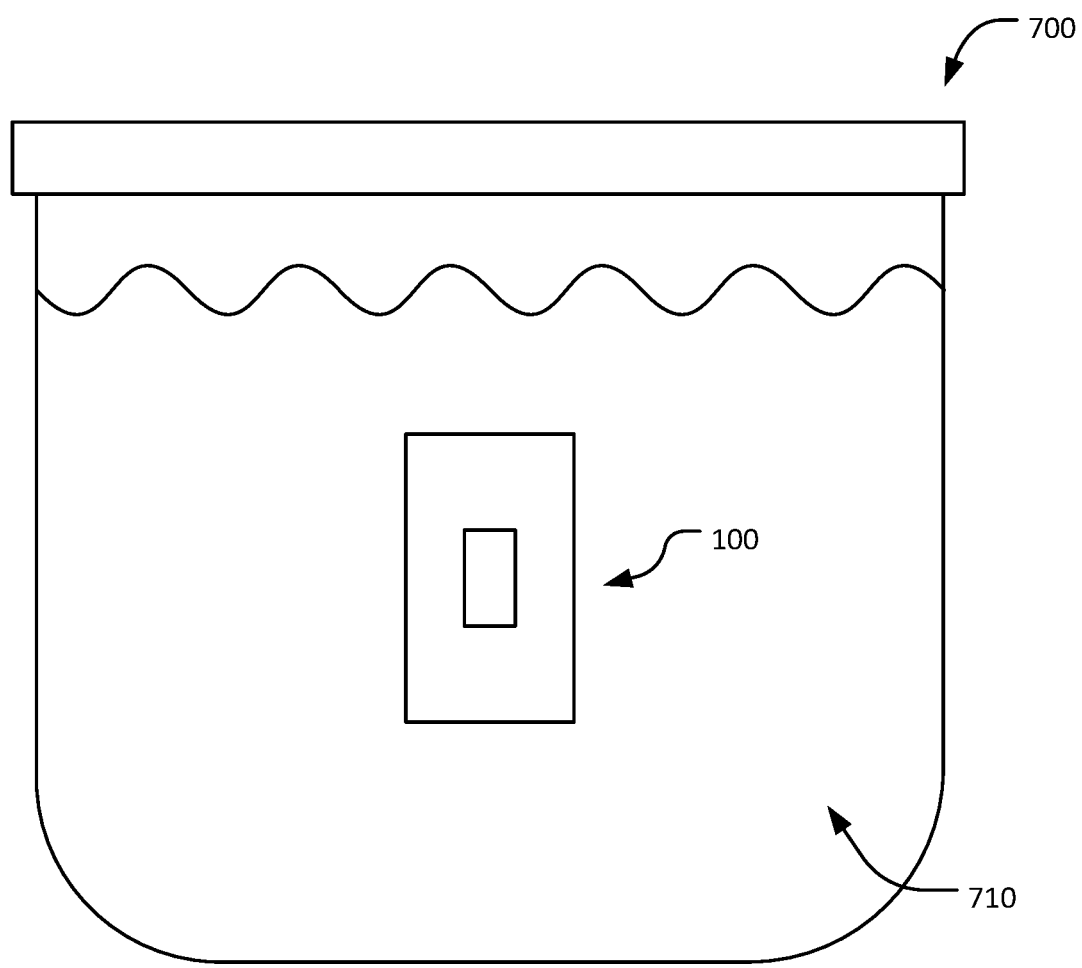
FIG. 7 shows an embodiment of a kitchen item with a monitor and indicator system.

FIG. 7 illustrates a sanitizer monitor 100 in use. Here, a container 700 may be filled with a sanitizing solution 710 and positioned near a food processing site. The sanitizing solution 710 may be used to sanitize kitchen utensils after use. A user may dispose a monitor and indicator system 100 (which may be a sticker) within the kitchen container 700 freely or in a fixed position. The monitor and indicator system 100 may immediately start working upon being in contact with the sanitizing solution (e.g., which may be powered by the electrical charges from the sanitizing solution). The monitor and indicator system 100 may continuously measure the concentration of the sanitizing compound element in the sanitizing solution 710 as described above. When the concentration of the sanitizing solution is above the predetermined concentration threshold, the monitor and indicator system 100 may activate the indication module 124 to emit a first notification (e.g., light indication, wired or wireless signal, dye, sound, etc.), or the system 100 may remain otherwise dormant. When the concentration of the sanitizing solution becomes equal to or falls below the predetermined concentration threshold, the monitor and indicator system 100 activates the indication module 124 to emit a second notification (e.g., light indication, wired or wireless signal, dye, sound, etc.) indicating that the sanitizing solution needs to be change. The kitchen personnel will see the notification, and subsequently replace the depleted sanitizing solution with a new batch of sanitizing solution having a concentration of the sanitizing chemical substance above the predetermined threshold concentration level. The kitchen personnel may dispose the used sticker monitor and indicator system 100 (or dispose a portion of the system 100 thereof, as the case may be) and insert a new monitor and indicator system 100 into the container 700.

In embodiments, a method for maintaining a concentration of a sanitizing solution may include the following steps: (a) providing a container; (b) filling the container with a sanitizing solution comprising a sanitizing chemical substance; (c) placing a first monitor and indicator system in or on the container, wherein the system has an adhesive area; (d) activating the monitor and indicator system to measure a concentration of the sanitizing chemical substance; and (e) activating the monitor and indicator system to emit a notification when the measured concentration of at least one sanitizing chemical substance is above a predetermined threshold concentration level, thus indicating a depleted sanitizing solution. The method may further include (f) replacing the depleted sanitizing solution with a new batch of sanitizing solution having a concentration of the sanitizing chemical substance above the predetermined threshold concentration level; (g) disposing of the first monitor and indicator system; and (i) placing a second monitor and indicator system on a surface of the kitchen container.

In other embodiments, a method for monitoring and indicating a concentration of a sanitizing solution may include the following steps: (a) providing a container; (b) filling the container with a sanitizing solution comprising a sanitizing chemical substance; (c) placing a monitor and indicator system with a sensor part, a control and indication part, and a power part in the container with the sanitizing solution; (d) activating the monitor and indicator system to measure a concentration of the sanitizing chemical substance; (e) activating the monitor and indicator system to emit a first notification when the measured concentration of the sanitizing chemical substance is above a predetermined threshold concentration level; (f) activating the monitor and indicator system to emit a second notification when the measured concentration of the sanitizing chemical substance becomes equal to or falls below a predetermined threshold concentration level, thus indicating a depleted sanitizing solution; (g) replacing the depleted sanitizing solution with a new batch of sanitizing solution having a concentration of the sanitizing chemical substance above the predetermined threshold concentration level; (h) disposing the monitor and indicator system; and (i) placing a new monitor and indicator system in the kitchen container with the new batch of sanitizing solution freely or in a fixed position.

In further embodiments, a method for monitoring and indicating a concentration of a sanitizing solution may include the following steps: (a) providing a container; (b) filling the container with a sanitizing solution comprising a sanitizing chemical substance; (c) providing a housing with a power part (e.g., battery) of a monitor indicator system including a sensor part and a control and indication part in the container with the sanitizing solution, wherein the parts are separable and the sensor part is disposable; (d) placing the housing with the power part in the container with the sanitizing solution freely or in a fixed position; (e) connecting the disposable sensor part and control and indication part of the monitor and indicator system to the housing by a connection socket; (e) activating the monitor and indicator system to measure a concentration of the sanitizing chemical substance; (f) activating the monitor and indicator system to emit a first notification when the measured concentration of the sanitizing chemical substance is above a predetermined threshold concentration level; (g) activating the monitor and indicator system to emit a second notification when the measured concentration of sanitizing chemical substance becomes equal to or falls below a predetermined threshold concentration level, thus indicating a depleted sanitizing solution; (h) replacing the depleted sanitizing solution with a new batch of sanitizing solution having a concentration of the sanitizing chemical substance above the predetermined threshold concentration level; (i) disposing the sensor part and control and indication part of the monitor and indicator system; and (j) connecting a new sensor part and a new control and indication part of the monitor and indicator system to the housing with the power part in the container with the new batch of sanitizing solution via the connection socket.

In embodiments, the monitor and indicator system 100 may be particularly useful in the food industries to monitor and/or indicate the concentration of a sanitizing chemical substance in a sanitizing solution for cleaning kitchen utensils, and to optionally send notifications when the concentration of the sanitizing compound element becomes equal to or falls below a predetermined level as described herein. For example, the sanitizing solution may be used to clean and sanitize surfaces that come into contact with food, such as knives, spoons, forks, and other utensils.

The sterilant may be one or more of the following chemicals: alcohol, formalin, glutaraldehyde, hydrogen peroxide, ozone, potassium permanganate, peroxyacid, phenolics, quaternary ammonium compounds, chlorine, hypo chlorite, hypochlorous acid, iodine, iodophors, sodium hydroxide, potassium hydroxide, calcium hydroxide, magnesium hydroxide, sulfurous acid, sulfur dioxide, thymol, pine oil, lactic acid, sodium bicarbonate, polyaminopropyl biguanide, diethylene glycol, benzethonium chloride, et cetera.

The monitor and indicator system 100 may be used to test, monitor, and/or indicate a chlorine concentration of a chlorine sanitizing solution, which may be prepared by adding chlorine or one or more chlorine compounds (e.g., sodium hypochlorite) to water. And the chlorine concentration may range from 10 to 200 ppm. Preferably, the upper chlorine concentration limit may be 200 ppm and the lower chlorine concentration limit may be 50 ppm. The threshold chlorine concentration may be set to between 10 and 200 ppm, and in embodiments, may be, for example, 50 ppm, 75 ppm, 100 ppm, 125 ppm, 150 ppm, or 175 ppm.

In embodiments, the monitor and indicator system 100 is used to test, monitor, and/or indicate a quaternary ammonium concentration of a quaternary ammonium sanitizing solution. And the quaternary ammonium concentration may range from 100 to 400 ppm. In embodiments, the upper quaternary ammonium concentration limit may be 200 ppm and the lower quaternary ammonium concentration limit may be 150 ppm. The threshold quaternary ammonium concentration may be set to between 100 and 400 ppm, and in embodiments, may be, for example, 100 ppm, 125 ppm, 150 ppm, 175 ppm, 200 ppm, 225 ppm, 250 ppm, 275 ppm, 300 ppm, 325 ppm, 350 ppm, 375 ppm, or 400 ppm.

In other embodiments, the monitor and indicator system 100 is used to test, monitor, and/or indicate an iodine concentration of an iodine sanitizing solution. And the iodine concentration may range from 5 to 50 ppm. In embodiments, the upper iodine concentration limit may be 25 ppm while the lower iodine concentration limit may be 12.5 ppm. The threshold iodine concentration may be set to between 5 and 50 ppm, and in embodiments, may be, for example, 5 ppm, 10 ppm, 15 ppm, 20 ppm, 25 ppm, 30 ppm, 35 ppm, 40 ppm, 45 ppm or 50 ppm.

As described briefly above, the monitor and indicator system may be a sticker having a generally rectangular shape. The length of the monitor and indicator sticker system may be 1 to 10 inches; the width of the monitor and indicator sticker system may be 0.5 to 5 inches, for example; and the depth of the monitor and indicator sticker system may be 0.1 to 5 inches, for example. In an exemplary embodiment, the length of the monitor and indicator sticker system may be 2 to 3 inches, and the width of the monitor and indicator system may be about 1 inch. Other shapes and configurations of the sticker are also contemplated within the scope of the invention.

During testing, it was determined that the quality of the water affects the ability of a testing device to accurately determine concentration. More specifically, when the water temperature, total dissolved solids (TDS), pH, and/or hardness level of the water is taken into account when determining a concentration of sanitizing solution, the results are far more accurate. Accordingly, in embodiments, a monitor and indicator system may be configured to operate in two modes: a calibration mode and an operational/measurement mode. As will be described in greater detail below, in the calibration mode, the testing device determines one or more characteristics of water without sanitizing solution. Subsequently, sanitizing solution/compounds are added to the water and the device enters the measurement mode to determine the concentration of the sanitizer in the water.

Figure 8:
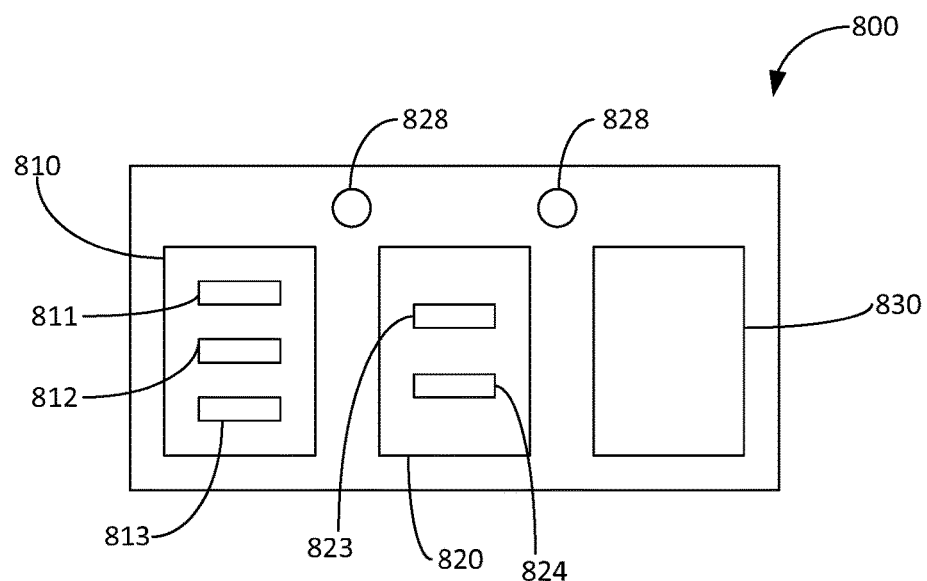
FIG. 8 is a schematic of another embodiment of a monitor and indicator system of the invention.
Figure 9:
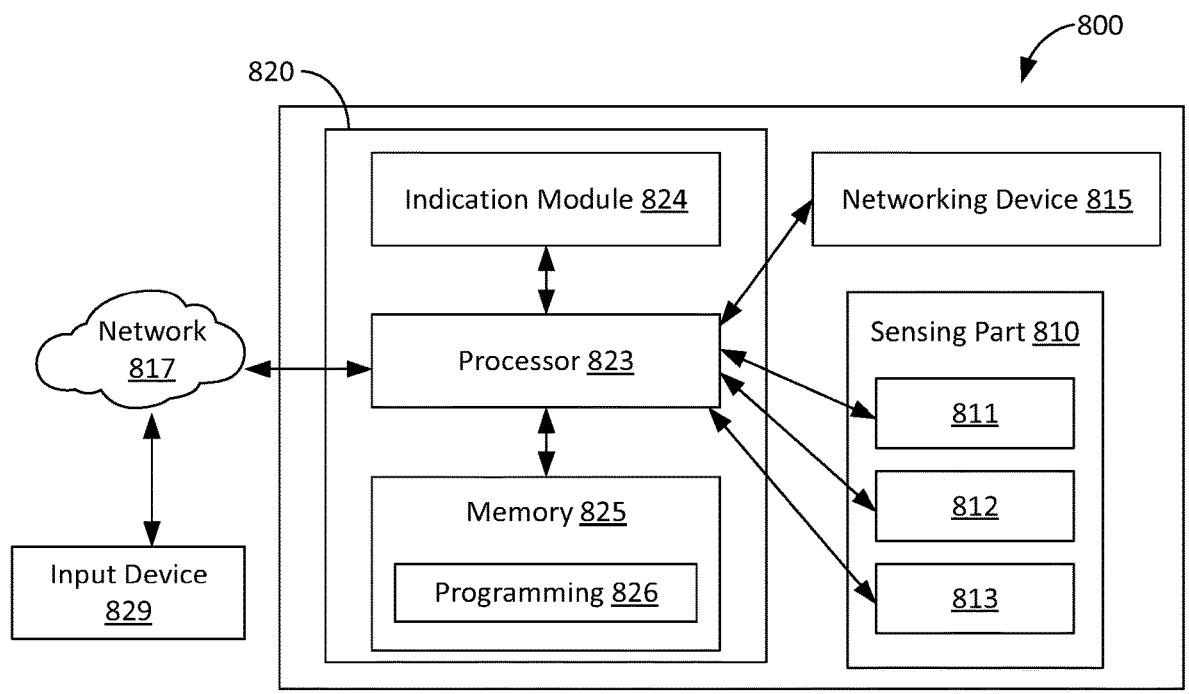
FIG. 9 is a schematic illustration of the processing system of the monitor and indicator system of FIG. 8.

FIGS. 8 and 9 generally illustrate a dual-mode monitor and indicator system 800 according to an embodiment of the invention. Generally speaking, the monitor and indicator system 800 may be similar to the monitor and indicator system 100. For example, the monitor and indicator system 800 may include a sensor part 810, a control and indication part 820, and a power part 830.

The sensor part 810 may include one or more sensors, e.g., 811, 812, and 813. While three sensors 811, 812, and 813 are shown in FIGS. 8 and 9, it shall be understood that additional or fewer sensors may be included within the sensor part 810. The sensors 811, 812, and 813 may include a temperature sensor, a pH sensor, a light sensor, a total dissolved solids (TDS) meter, a water hardness meter, and/or a sensor for determining the concentration of a sanitizer in a sanitizing solution. The sensor for determining the concentration of sanitizer in solution may be any sensor now known or later developed, such as an inductive conductivity sensor as described herein. The conductivity sensor may include analog sensing circuitry and may be configured to measure resistance of the solution which can be used to calculate the concentration as is known to those of skill in the art.

The control and indicator part 820 may include a processor 823, an indication module 824, and memory 825 housing software (also referred to herein as programming) 826 for controlling operations of the device 800. Processor 823 represents one or more digital processors. In some example embodiments, the processor 823 may be configured through particularly configured hardware, such as an application specific integrated circuit (ASIC), field programmable gate array (FPGA), etc., and/or through execution of software to perform functions in accordance with the disclosure herein.

Memory 825 represents one or more of volatile memory (e.g., RAM) and non-volatile memory (e.g., ROM, FLASH, magnetic media, optical media, etc.). Although shown within the control and indicator part 820, memory 825 may be, at least in part, implemented as network storage that is external to the control and indicator part 820 and accessed via a network interface. Programming 826 may be stored in a transitory or non-transitory portion of the memory 825. Programming 826 includes machine readable instructions that are executed by the processor 823 to perform the functionality of the device 800 as described herein.

The processor 823 may be in operable communication with the memory 825, the indication module 824, the sensor part 810 (more specifically, with the sensors 811, 812, and 813), a networking device 815, and an input device 829. The processor 823 is configured to, in conjunction with the programming 826, receive information from the one or more sensors 811, 812, and 813, process the information, and provide a corresponding response via the indication module 824. As is described herein, the concentration determination may be affected by the temperature of the water, the TDS, the pH and/or the hardness of the water. Accordingly, the sensors 811, 812, and 813 (e.g., temperature sensor, TDS meter/sensor, pH sensor, and/or electronic water hardness meter) inform the programming 826, and the programming 826 utilizes the information, along with information from e.g., the conductivity sensor, to make a more accurate concentration determination.

The indication module 824 may include one or more lights, though other indicators may additionally or alternately be used (e.g., speakers, dye, etc.), and is configured to activate upon the programming 826 determining that the concentration of the sanitization solution is outside of a predetermined threshold. The indication module 824 may be activated when the sanitization concentration is above, at, and/or below the predetermined threshold.

The networking device 815 may be configured to allow the device 800 to communicate over wired and/or wireless networks; for instance, as shown in FIG. 8, the networking device 815 may allow the device 800 to communicate with the input device 829 over a network 817 (e.g., a Wi-Fi, Internet, Bluetooth, or other wired or wireless network).

The input device 829 may have the appropriate hardware and/or software such that the input device 829 can communicate with the device 800 over the network 817. In embodiments, the input device 829 may be hardwire connected to the device 800 rather than in a network connection with the device 800. The input device 829 may be, for example, a scanner, such as a one-dimensional code barcode or a two-dimensional QR code scanner. The input device 829 may additionally, or alternatively, include a computer mouse, camera, keyboard, any other input device now known or developed in the future, and the input device 829 may include a user interface. For example, the input device 829 may be a computer that includes a keyboard and/or a mouse. The input device 829 may be provided in order to supply additional and/or alternative information to the device 800. As described below, the memory 825 may include threshold values for various sanitizing compounds such that the device 800 can determine how and/or when to activate the indication module 824. The processor 823 may access the memory 825 to access the saved threshold values. In embodiments, the device 800 may be able to analyze what sanitizing compounds are used in water without the input device 829 having to provide the information. However, in other embodiments, the input device 829 may be used to tell the device 800 what sanitizing compounds are being used such that the correct threshold values can be accessed in the memory 825. For example, a sanitizing compound (e.g., packet) may include a barcode, and the input device 829 may be configured as a scanner. When a user is preparing a sanitizing solution, he may utilize the scanner 829 to scan the barcode associated with the sanitizing compound. This information is then used by the processor 823 to access the thresholds from the memory 825 that correspond to that particular sanitizing compound. In another example, the input device 829 is a computer. The user may utilize the computer mouse and/or keyboard to tell the device 800 what sanitizing compound is being used such that the device 800 can access the thresholds from the memory 825 that correspond to that particular sanitizing compound.

The input from the input device 829, and particularly information regarding the sanitizing compounds used, may additionally or alternately be used by the programming 826 in determining whether the sanitizing solution meets the corresponding threshold values. Sanitizing compounds from different manufacturers may have different active ingredients (or different ratios of active ingredients), even if the sanitizing compounds are largely the same. For example, although two products may be marketed as a quaternary ammonia sanitizer, one may have 9.28% active ingredients while another may have 23.08% active ingredient. The percentage of the active ingredient may impact how the device 800 determines whether the sanitizing solution is within required thresholds. Accordingly, the device 800 may need to know with specificity the characteristics of the product being used. The input device 829 may be used as described above to tell the device 800 what the product is (e.g., scanning a barcode tells the device 800 the manufacturer of the product). The memory 825 may house information related to specific sanitizing compounds from various manufacturers such that the device 800 can access the information about the compounds and utilize it within the programming 826. Additionally or alternately, the device 800 may utilize the network 817 to retrieve information about the specific sanitizing compound for use with the programming 826.

Finally, the power part 830 may include one or more batteries for providing power to the device 800. As described above, the power part 830 may alternatively or additionally be provided as an internal electrochemical source, power interface, and/or any other means of providing power to the system 800.

The monitor and indicator system 800 may be embodied in a single device, i.e., the sensor part 810, the control and indicator part 820, and the power part 830 are all arranged in and/or on a single housing. The monitor and indicator system 800 may therefore function as a comprehensive appliance that conducts a water analysis of a clean water sample and monitors a concentration of a sanitizing solution once sanitizing compound(s) is added to the water without requiring the appliance to be removed from the water or adjusted by the user. Of course, the device 800 may be removed from the clean water prior to being placed in a sanitizing solution. The device 800 may be designed to float in water/sanitizing solution. However, in alternative embodiments, the device 800 may be embodied as a clip (e.g., to clip onto a side of a container), a sticker (e.g., as described above), or any other instrument that allows the device 800 to operate in accordance with the description provided herein.

General operation of the monitor and indicator device and system 800 is now described with reference to the foregoing figures and explanation. The system 800 begins operation by the programming 826 running a self-diagnostic program to check the status of the various sensors 811, 812, and 813. Once it is confirmed that the sensors 811, 812, and 813 are operational, analog sensing circuitry associated with the means for determining concentration may undergo a calibration routine utilizing a test fixture to create offset and gain correction factors to reduce variation between devices. As the initial self-diagnostic program is run, power may be provided via a wired power supply, though other power supplies may additionally or alternatively be used.

Once the initial self-diagnostic calibration is complete, a more permanent power supply (e.g., one or more batteries 830) may be installed into the device 800. Optionally, the battery 830 may be installed prior to the initial self-diagnostic calibration step. Regardless, the processor 823 may initiate a second self-diagnostic routine via the programming 826. Optionally, the circuit calibration routine may be skipped. The device 800 may then enter a sleep mode.

In the sleep mode, the device 800 may operate in a reduced-capacity, low-powered state. The device 800 may be programmed to operate in the sleep mode for a predetermined period of time (e.g., 10 minutes, 30 minutes, 1 hour, 2, hours, 1 day, etc.), which may allow for the device 800 to be packaged in a light-proof package such that the device 800 is not prematurely awoken from the sleep mode.

Once the device 800 is in the packaging and the predetermined period for the sleep mode has expired, the device 800 enters into a wait state. In the wait state, the device 800 remains in a low-powered state. One or more light sensors may include an interrupt configured to wake the device 800 when light is detected.

When the device 800 wakes from the wait state, it may enter a baseline wake state. In the baseline wake state, one or more lights within the device 800 (e.g., one or more lights in the indication module 824) may blink, e.g., in a particular pattern, to provide an indicator that the device 800 is waiting to enter calibration mode. To enter calibration mode, probes 828 on the device 800 (e.g., using a key, specifically designed cradle, or other effective means) are shorted, which may require contact to be established between the probes for a period of time (e.g., 5 seconds, 10 seconds, 15 seconds, etc.). The device 800 may provide a signal (e.g., blinking lights) to alert a user that the device 800 has successfully entered calibration mode, at which time the device 800 begins a method for monitoring the concentration of a sanitizing solution. If the device 800 does not enter calibration mode within a predetermined period of time (e.g., 5 minutes, 10 minutes, 15 minutes, etc.), the device 800 may return to the wait state or a semi-wait state so as not to waste battery power.

Figure 10:
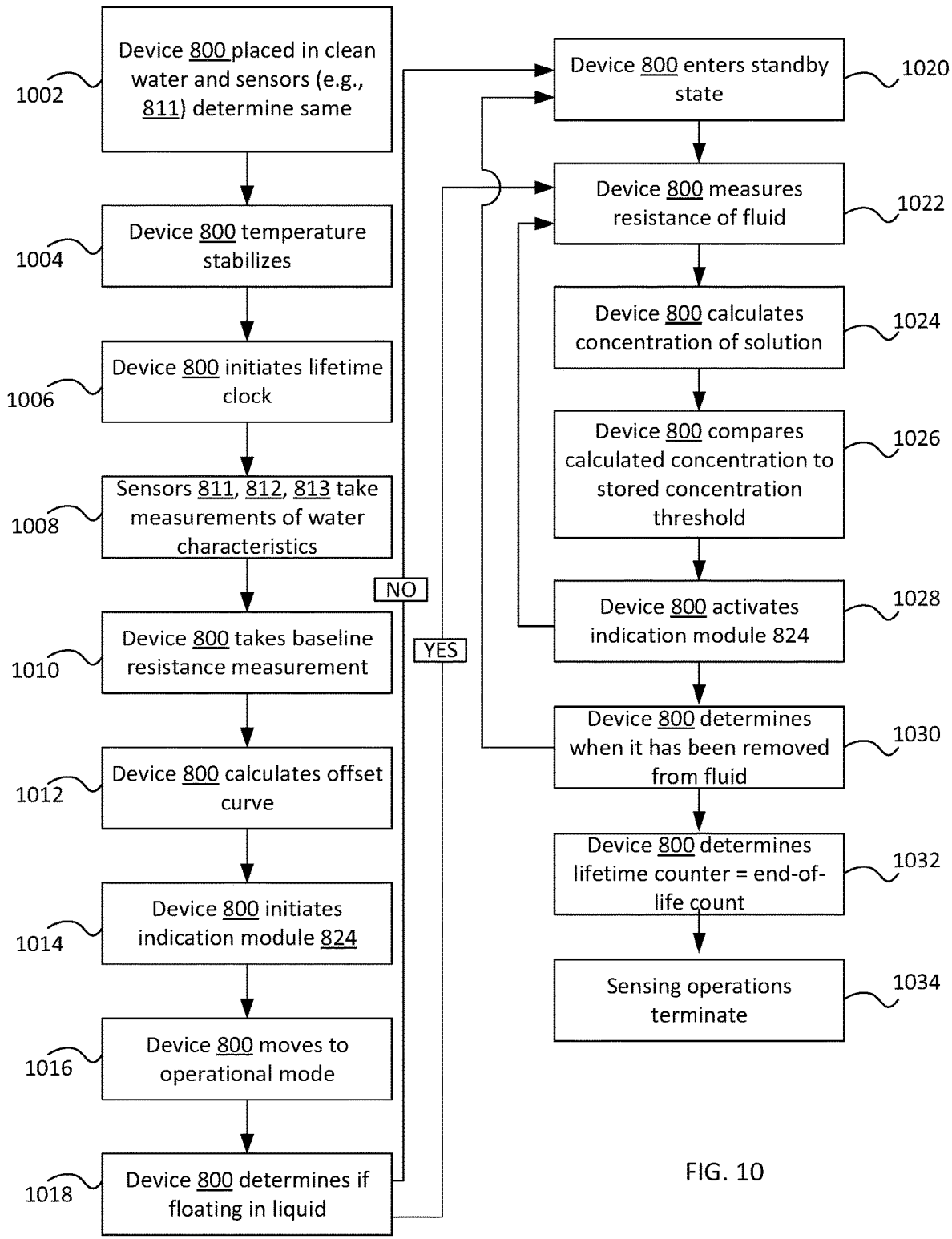
FIG. 10 is a flowchart illustrating steps for monitoring a sanitizing solution according to embodiments of the invention.

A method of monitoring the concentration of a sanitizing solution according to an embodiment of the invention is illustrated in FIG. 10. The method begins at step 1002, where the device 800 is in calibration mode (after shorting the probes, as mentioned above). At step 1002, the device 800 is put into clean water and the processor 823 via sensors 811, 812, 813 and programming 826 determines that the device 800 is in clean tap water. At step 1004, the device 800 temperature stabilizes (e.g., the temperature of the device 800 comes to equilibrium with the water temperature). The wait time may be preprogrammed, or the device 800 may automatically determine (e.g., via a series of temperature measurements) that the temperature has stabilized. Generally concurrently with step 1004, at step 1006, the device 800 via programming 826, may initiate a lifetime clock. The process then moves to step 1008.

At step 1008, the device 800, via sensors 811-813, conducts a water analysis. To conduct the water analysis, the sensors 811-813 may take one or more measurements of the water including but not limited to pH, TDS, dissolved oxygen, chlorine concentration, alkalinity, and/or hardness. It shall be understood that, if it is desired to determine TDS as part of the water analysis, a TDS meter as is traditionally understood may be incorporated into the device 800 and utilized accordingly. Alternatively, the TDS in the water may be determined by measuring the electrical conductivity (EC) of the water and correlating the EC to the TDS of the water sample. It is generally understood that EC and TDS may be correlated according to the equation:

$$TDS(mg/L) = k_e \times EC(\mu S/cm) \tag{1}$$

where $k_e$ is a constant of proportionality (typically assumed to be 0.7 for EC be 75,000 μS/cm) and the water temperature is at or near room temperature (i.e., approximately 25° C. or 77° F.).

Optionally, the measurements taken at step 1008 may be stored in memory 825. At step 1010, the analog sensing circuitry takes a baseline resistance measurement, and the measurement may be stored in memory 825. The programming 826 utilizes the baseline resistance measurement to calculate an offset curve for the water sample at step 1012. Then at step 1014, the programming 826 may initiate the indication module 824 to cause one or more of the lights to blink, e.g., according to a pattern, to alert the user that the baseline measurements are complete. The device 800 then moves from the calibration mode to the operational mode at step 1016.

Moving on, at step 1018, the device 800 determines if it is floating in liquid (e.g., via sensor readings). If the device 800 determines that it is not floating in liquid, then the process moves to step 1020. At step 1020, the programming 826 may cause the device 800 to enter into a low-power standby state. In the low-power standby state, the programming 826 may cause one or more of the lights to blink and/or one or more of the sensors 811, 813, 813 to take a reading according to a preset schedule, e.g., every 1, 2, 5, 10, 20, 30, etc. seconds. If the device 800 receives a calibration signal (e.g., the probes are shorted), then process returns to step 1002. However, if the device 800 detects that it is in liquid, then the process moves to step 1022. If at step 1018 the device 800 determines that it is floating in liquid, then the process moves directly to step 1022.

At step 1022, the programming 826 causes the analog sensing circuitry to test resistance of the fluid. The resistance may be taken at predetermined time intervals (e.g., every 1, 2, 5, 10, 20, 30, etc. seconds. With the resistance measurements, the programming 826 calculates the concentration of the solution at step 1024. The calculation of the concentration of the solution takes into account the measurements and/or determinations made during the calibration mode, namely, the water temperature, pH, TDS, hardness, baseline offset and/or battery voltage. This ensures that the concentration is as accurate as possible. The process then moves to step 1026.

At step 1026, the programming 826 compares the calculated concentration with threshold values (e.g., stored in memory 825). At step 1028, the programming 826 initiates the indication module 824. If the programming 826 determines that the solution concentration is below a low threshold value, the programming 826 may cause one or more of the lights (e.g., in the indication module 824) to blink a particular color (e.g., red). If the programming 826 determines that the solution concentration is between low and high threshold values, the programming 826 may cause one or more of the lights (e.g., in the indication module 824) to blink a particular color (e.g., green). And if the programming 826 determines that the solution concentration is above the high threshold value, the programming 826 may cause one or more of the lights (e.g., in the indication module 824) to blink a particular color (e.g., yellow). Of course, there may be separate lights and the programming 826 may activate the correct light depending on the determination. Furthermore, the device 800 may be specific to a particular sanitizing substance (e.g., quaternary ammonia) such that the threshold values stored in memory 825 are specific and limited to that substance. In other embodiments, multiple threshold values may be stored in the memory 825 and a user may activate the device 800 based on the specific sanitizing substance such that the programming 826 compares the calculated concentration to the correct threshold values. Steps 1022-1028 can be repeated any number of times, at which point the process moves to step 1030.

At step 1030, the device 800 determines when it has been removed from fluid (e.g., via sensor readings). The process then returns to step 1020, and may repeat as described above.

Moving on, at step 1032, the programming 826 determines if the lifetime counter is equal to the end-of-life count (e.g., stored in memory 825). The end-of-life count may be equal to, e.g., 1 day, 10 days, 100 days, 1 year, 5 years, et cetera. If the lifetime counter is equal to the end-of-life count, the process then moves to step 1034, where sensing operations are terminated. The programming 826 may cause lights (e.g., in the indication module 824) to blink periodically (e.g., red and yellow) until the battery voltage falls below an operational threshold, at which point all operations may cease. The process is then complete, and may begin again with a new device 800.

Any time the device 800 determines that the probe pins are shorted, the process returns to step 1002, and the device 800 reenters calibration mode.

Examples

Active chlorine is difficult to measure at high levels (e.g., greater than 50 ppm). Test strips are known to be inaccurate, and alternative methods of monitoring chlorine levels, such as ion-specific electrodes, are expensive and subject to contamination-induced errors. An experiment was designed to test active chlorine levels in a solution that contains chlorine bleach from sodium hypochlorite solutions or organic chlorine sources (e.g., sodium dichloroisocyanurate). Hypochlorite is a strong oxidizer; accordingly, the electrical properties of the solution were studied.

Electrodes (Cu cathode, Zn anode) were placed in a sanitizer solution containing an active chlorine source. The theoretical potential for the Cu/Zn electrode couple is 1.10 volts direct current (VDC). In the solution, the electrode a measured voltage of 0.95 volts direct current (VDC) and a current of about 15-20 mAmps. Without an active chlorine source, such as sodium dichloroisocyanurate, the measured voltage of the solution is approximately equal to the solution with the active chlorine source; however, the current produced is significantly lower, measuring at below 2 mAmps.

The low current produced in the non-active chlorine solution is likely due to the reaction of the Zn anode with the alkaline solution, which likely forms zinc hydroxide. In the active chlorine solution, the higher levels of current measured is believed to be due to oxidation of the zinc anode by the sodium hypochlorite. Although the concentration of the sodium hypochlorite was not specifically measured, the current produced due to the oxidation of the Zn is proportional to the hypochlorite concentration. Similarly, the amount of current produced is proportional to the surface area of the anode.

Several experiments were conducted for various solution compositions. Distilled water having a pH of between 6.2 and 6.8 was used in all measurements. Measurements were taken at room temperature, ranging from about 18.5-19.5 degrees Celsius. The measured voltage of the distilled water ranged from 0.85 to 0.9 VDC, with no current measured. The surface area of the electrodes was about 6 square inches. The base solution is a propriety sanitizing solution manufactured by Purdy®, and contains all sanitizing components except sodium dichloroisocyanurate. The sodium dichloroisocyanurate was procured from Purdy for addition to the test solutions. The pH of the base solution was 10.5 to 11.0. After addition of the chlorine source, the pH of the solution was reduced about ½ to 1 pH unit.

Without the chlorine source, the sanitizing solution had a pH of about 11.0. the measured voltage was 0.95 VDC and the measured current was 0.5 to 1.5 mAmp. With the chlorine source, the sanitizing solution had a pH of 10.5, the measured voltage was 0.94 VDC, and the measured current was 18 mAmp+/-2 mAmp. The measured current was observed to be somewhat unstable unless the solution was stirred.

Addition of the chlorin source to the base solution provided noticeable changes in the measured current which appears to be proportional to the amount of the chlorine source added. In several instances, it was observed that the measured current was nearly double when the amount of chlorine doubled.

The electrodes may experience polarization over time. In a static system without agitation, a charged layer of ions may build up at the surface of the electrodes. This may inhibit diffusion of the reactants thereby slowing the reaction at the surface of the electrodes causing inaccurate readings. To create a dynamic system, a magnetic stirrer was used to maintain agitation in the system which appeared to minimize the effect of polarization and allow stable current readings.

In addition to polarization, contamination of the surface of the anode (Zn) with reaction products (e.g., ZnO) may occur. The contamination was observed as a buildup of white precipitate on the surface of the anode.

Hypochlorite in the solution is consumed at the anode. This reaction produces the current used to determine the hypochlorite concentration. It is believed that there is not enough hypochlorite consumed to interfere with the overall performance of the system. This is because, in the system, there is equilibrium among the parent compound (sodium dichloroisocyanurate) and the various species of hypochlorite compounds. As hypochlorite is consumed at the anode, more is "released" by the sodium dichloroisocyanurate. This equilibrium helps to maintain the level of hypochlorite in the solution.

Surface contamination of the anode may result in a lower current reading. Contamination may be due to build of food stuffs in the solution (e.g., fats, oils, particulates). It is believed that by the time this buildup is significant enough to have an effect on the readings that it will be desirable by the user to change the solution based on the dirty nature of the water regardless of any reading.

Based on the observed results, it can be determined that the concentration of the hypochlorite in the solution may be indirectly followed via the current produced by a galvanic cell.

FIGS. 11a and 11b illustrate results from various experiments taken in multiple locations showing the effect of water hardness and temperature on concentration. All of the experiments were conducted under similar conditions. The actual PPMs were determined at room temperature (21.1° C./70° F.) and through titration. In each case, the sanitizer used was quaternary ammonia. The counts listed in each of the tables correspond to an electronic pulse that measures resistance. The counts were determined by an analog-to-digital converter, and are used to determine the concentration of the sanitizing solution. The counts are dependent on the other information, including TDS and temperature. In other words, a certain count can be determined to reflect a certain concentration of solution if the programming 826 knows the baseline TDS and temperature of the water source without sanitizing solution.

The Device Temp corresponds to the temperature of the device 800, and the Thermo Temp corresponds to the temperature of the water as determined by a thermometer. As the device sits in the water, the device temperature will eventually equalize to the temperature of the water. In the experiments represented in FIGS. 11a and 11b, the counts are related to the Thermo Temp, as this is a more accurate reading of the temperature of the water at the time the readings were taken.

The Thermo Temps and the counts recorded for each of the Cold Tests, Warm Tests, and Hot Tests can be utilized to develop temperature curves which are utilized by the programing to inform the concentration calculation.

The experiments represented in the tables in FIGS. 11a and 11b help to inform the programming 826 regarding the concentration calculation. The data is provided to the programming 826 to develop algorithms such that the device can make concentration determinations. For example, in the experiment LS #2, the device determined the count to be 1998. Through titration it was determined that the Actual PPM of the sanitizer in the solution was 414 PPM (even though the amount of sanitizer used according to package instructions should have been nearer 450 PPM). The data therefore suggests that the count 1998 represents a concentration of 414 PPM at a temperature of 19.4° C. at a water hardness level of 28. The device 800, via programming 826, can then translate that count at similar temperatures and water hardness as representing approximately 414 PPM of sanitizer in the solution.

In the experiment FGS #4, the hardness level of the water was measured at 203, vastly different than the hardness level of the water in experiment LS #2. It can be seen that the counts measured in experiment FGS #4 are similarly significantly different than the counts measured in experiment LS #2. Therefore, the data suggests that the count 582 represents a concentration of 397.3 PPM at a temperature of 19.8° C. at a water hardness level of 203. Again, the device 800 is configured such that the programming 826 can translate such counts taken at similar temperatures and water hardness as representing a concentration of approximately 400 PPM.

Figure 12:
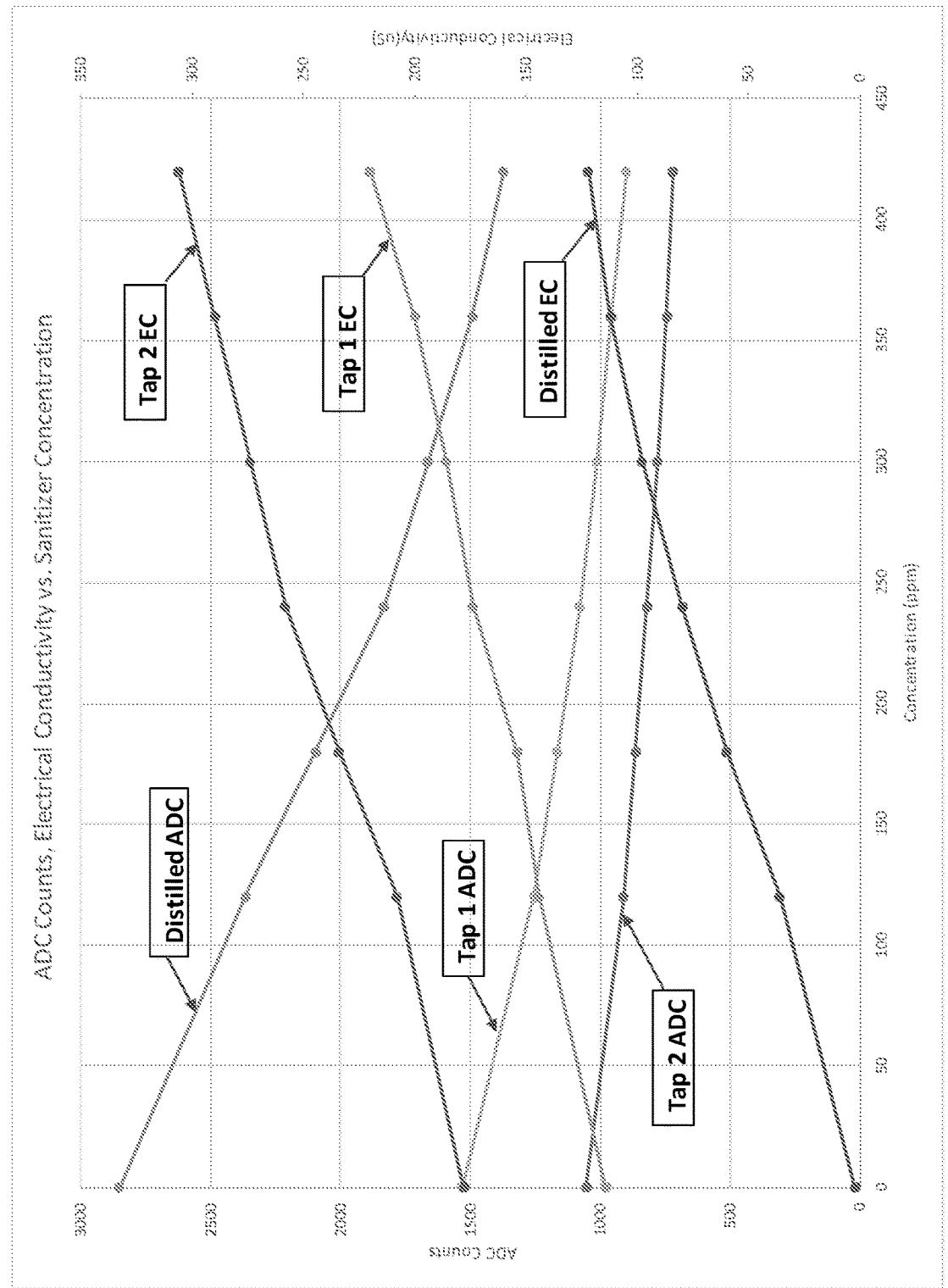
FIG. 12 is graph showing total dissolved solids and counts versus concentration.

FIG. 12 is a plot showing ADC counts and electrical conductivity (µS) versus concentration of sanitizing solution (in this case, quaternary ammonia compounds (QACs)) according to six experiments. In each case, as the concentration increases, the counts decrease. For example, the Distilled ADC experiment shows that when the concentration was zero PPM (e.g., no sanitizer compounds in the water) the count was measured at approximately 2900. At a concentration of approximately 425 PPM QACs, the count was measured at approximately 1400. Conversely, as the concentration increases, the EC of the solution increases. Referring again to the Distilled experiment, the line labeled Distilled EC, when the concentration was zero PPM (e.g., no QACs in the water) the EC measured zero as expected, indicating the lack of organic and inorganic substances in the distilled water. As the concentration of QACs in the water increases, the EC of the solution also increases as a result of the presence of the QACs in the water. In essence, counts are a function of concentration of QACs in the water. However, if this were the full story, then the counts would be the same regardless of the water source. That is clearly not the case, as the count measured at zero concentration for line labelled Tap 2 ADC, approximately 1500, is significantly lower than the Distilled Water ADC. The counts are therefore also influenced by the of the water characteristics of the water source (e.g., pH, TDS, hardness, alkalinity, temperature, chlorine content, dissolved oxygen content, et cetera). It should be mentioned that Tap 2 ADC and Tap 2 EC contain data points taken from the same water source at a set temperature. Similarly, Tap 3 ADC and Tap 3 EC contain data points taken from the same water source at a set temperature. Based on this information, the programming 826 can make a concentration determination wherein the concentration is derived from the solution resistance measurement, compensating for temperature and baseline TDS.

Many different arrangements of the various components depicted, as well as components not shown, are possible without departing from the spirit and scope of the present disclosure. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

What is claimed is:

1. A device for monitoring a concentration of sanitizing compounds in water, comprising:
a power module;
a sensor part comprising a plurality of sensors; and
a control and indicator part, comprising:
a processor in operable communication with an indication module and non-transitory computer memory having programming that, when executed by the processor, performs the following steps:
executing a calibration stage, comprising:
determining, via at least one sensor of the plurality of sensors, a temperature of a sample of water from a water source, the sample of water being devoid of sanitizing compounds;
measuring, via at least one sensor of the plurality of sensors, a characteristic of the sample of water; and
measuring, via at least one sensor of the plurality of sensors, a baseline resistance of the sample of water; and
executing an operational stage, comprising:
determining a resistance of a sanitizing solution, wherein the sanitizing solution comprises water from the water source and at least one sanitizing compound;
calculating a concentration of the sanitizing solution, wherein the concentration is based on the temperature of the water sample, the characteristic of the water sample, and the baseline resistance of the water sample;
comparing the calculated concentration to a predetermined threshold concentration stored in the memory; and
activating the indication module based on the comparison of the calculated concentration to the predetermined threshold concentration.

2. The device of claim 1, wherein the plurality of sensors comprises at least a temperature sensor and a conductivity sensor.

3. The device of claim 2, wherein the indication module comprises at least one light.

4. The device of claim 1, wherein the activating the indication module step comprises:
(i) causing a first indicator to activate if the calculated concentration is below a low threshold value of the predetermined threshold concentration;
(ii) causing a second indicator to activate if the calculated concentration is between the low threshold value and a high threshold value of the predetermined threshold concentration; and
(iii) causing a third indicator to activate if the calculated concentration is above the high threshold value of the predetermined threshold concentration.

5. The device of claim 1, wherein the at least one sanitizing compound comprises quaternary ammonia compounds (QACs).

6. The device of claim 1, wherein the calibration stage further includes activating a lifetime clock, and the operational stage further includes determining if the lifetime clock equals a predetermined end-of-life count.

7. The device of claim 6, wherein the operational stage is repeated until the lifetime clock equals the predetermined end-of-life count.

8. The device of claim 1, wherein the device returns to the calibration stage if probe pins on the device are shorted.

9. The device of claim 1, wherein the characteristic of the water is at least one characteristic selected from the list consisting of total dissolved solids, conductivity, alkalinity, chlorine content, dissolved oxygen content, pH, and hardness.

10. A method of monitoring a concentration of sanitizer in a solution, comprising:
providing a device for monitoring a concentration of a sanitizing solution, comprising a plurality of sensors;
executing, via the device, a calibration stage, comprising:
placing the device in water, the water being devoid of sanitizer, wherein the device:
determines a temperature of the water;
conducts a water analysis; and
measures, via at least one sensor of the plurality of sensors, a baseline resistance of the water; and
adding sanitizing compounds to the water; and
executing, via the device, an operational stage, wherein the device:

determines a resistance of the water with the sanitizing compounds;

calculates a concentration of the sanitizing compounds in the water, wherein the concentration is based on the temperature of the water, the water analysis, and the baseline resistance;

compares the calculated concentration to a predetermined threshold concentration; and activates an indication module of the device based on the comparison of the calculated concentration to the predetermined threshold concentration.

11. The method of claim 10, wherein activation of the indication module comprises:
(i) activating a first indicator if the calculated concentration is below a low threshold value of the predetermined threshold concentration;
(ii) activating a second indicator if the calculated concentration is between the low threshold value and a high threshold value of the predetermined threshold concentration; and
(iii) activating a third indicator if the calculated concentration is above the high threshold value of the predetermined threshold concentration.

12. The method of claim 11, wherein the first indicator, the second indicator, and the third indicator are embodied in a single indicator source.

13. The method of claim 12, wherein the operational stage is repeated according to a predetermined schedule.

14. The method of claim 12, wherein, in the operational stage, the device further determines whether the device is floating in liquid.

15. The method of claim 14, wherein the operational stage is repeated until the device determines that the device is not floating in liquid.

16. The method of claim 10, wherein the characteristic of the water is at least one characteristic selected from the list consisting of total dissolved solids, conductivity, alkalinity, chlorine content, dissolved oxygen content, pH, and hardness.

17. A method of monitoring a concentration of sanitizing compounds in a solution, comprising:

providing a device for monitoring a concentration of a sanitizing solution, comprising:
a power module;
a sensor part comprising a plurality of sensors; and
a control and indicator part;

executing a calibration stage, comprising:
placing the device in water, the water being devoid of sanitizer, wherein the device:
determines a temperature of the water;
measures, via at least one sensor of the plurality of sensors, a value of electrical conductivity of the water; and
measures, via at least one sensor of the plurality of sensors, a baseline resistance of the water; and
adding at least one sanitizing compound to the water; and executing an operational stage, wherein the device:
determines a resistance of the water with the at least one sanitizing compound;
calculates a concentration of the at least one sanitizing compound in the water, wherein the concentration is based on the temperature of the water, the electrical conductivity of the water, and the baseline resistance of the water;
compares the calculated concentration to a predetermined threshold concentration; and
activates the indication module based on the comparison of the calculated concentration to the predetermined threshold concentration.

18. The method of claim 16, wherein:
in the calibration stage, the device further determines a hardness level of the water; and
in the operational stage, the calculated concentration is further based on the hardness level of the water.

19. The method of claim 17, wherein:
in the calibration stage, the device further determines a pH of the water; and
in the operational stage, the calculated concentration is further based on the pH of the water.

20. The method of claim 17, wherein the operational stage is repeated according to a predetermined schedule.

* * * * *